(12) United States Patent
Blake et al.

(10) Patent No.: US 10,342,223 B2
(45) Date of Patent: Jul. 9, 2019

(54) MOLLUSK WITH COATED SHELL

(71) Applicant: Glofish, LLC, Earth City, MO (US)

(72) Inventors: Alan Blake, Austin, TX (US); Richard Crockett, Wilton, CT (US)

(73) Assignee: GloFish, LLC, Earth City, MO (US)

( * ) Notice: Subject to any disclaimer, the term of this patent is extended or adjusted under 35 U.S.C. 154(b) by 1052 days.

(21) Appl. No.: 14/177,362

(22) Filed: Feb. 11, 2014

(65) Prior Publication Data

US 2014/0224182 A1    Aug. 14, 2014

Related U.S. Application Data

(60) Provisional application No. 61/764,403, filed on Feb. 13, 2013.

(51) Int. Cl.
*A01K 63/00* (2017.01)
*A01G 5/06* (2006.01)
*A01K 67/033* (2006.01)

(52) U.S. Cl.
CPC ........ *A01K 67/0331* (2013.01); *A01K 63/006* (2013.01)

(58) Field of Classification Search
CPC ......... A22C 29/00; A22C 29/02; A22C 29/04; A01K 63/006; A01K 67/0331

USPC ....... 119/200, 201, 204, 205, 213, 214, 234, 119/269; 427/4

See application file for complete search history.

(56) References Cited

U.S. PATENT DOCUMENTS

| | | | |
|---|---|---|---|
| 2,080,263 A * | 5/1937 | Gibson | A23L 1/33 426/231 |
| 3,836,765 A | 9/1974 | Ritzow et al. | |
| 5,089,940 A | 2/1992 | Lanzarone et al. | |
| 7,135,613 B1 | 11/2006 | Gong et al. | |
| 7,700,825 B2 | 4/2010 | Blake et al. | |
| 7,834,239 B2 | 11/2010 | Gong et al. | |
| 2005/0034677 A1 | 2/2005 | Blake et al. | |
| 2008/0316732 A1 | 12/2008 | Blake | |
| 2009/0006219 A1 | 1/2009 | Blake et al. | |

OTHER PUBLICATIONS

THe Mollusks: A Guide to Their Study, Collection, and Preservation—Charles Sturm et al 2006.*

* cited by examiner

*Primary Examiner* — Richard T Price, Jr.
(74) *Attorney, Agent, or Firm* — Merchant & Gould P.C.

(57) ABSTRACT

Embodiments of the present invention relate to mollusk with fluorescent coatings. Also disclosed are aquarium kits comprising a tank, mollusk and an excitation light source.

19 Claims, 4 Drawing Sheets

MOLLUSK WITH COATED SHELL

CROSS-REFERENCE TO RELATED APPLICATIONS

This application claims priority to U.S. Provisional Patent Application Ser. No. 61/764,403, filed Feb. 13, 2013, the contents of which are incorporated by reference herein

BACKGROUND OF THE INVENTION

1. Field of the Invention

This invention relates to mollusks with a coating applied to an external shell, as well as aquarium kits comprising such mollusks.

2. Description of Related Art

Aquariums are typically comprised of a tank which can be filled with water, a system for maintaining the condition of the water (e.g. filter, aeration pump, heater), and ornamental features such as plants, gravel, rocks and curios. The tank may be of any shape such as rectangular tanks or round bowls, and the sides of the tank are typically transparent. The aquarium may also be provided with a lighting system. Aquariums are typically used to display fish, mollusks, and other aquatic species.

Certain aquarium systems have been configured to optimize the visual display of the contents, including the aquatic species contained within. Various aquarium lighting systems have been previously shown and described. For example, U.S. Pat. Nos. 3,836,765 and 5,089,940 describe lighting systems comprising a hood and a lighting fixture housed in the hood. The hood is configured to rest on the top of an aquarium tank.

Certain aquatic species have also been optimized for appearance under specific conditions present in specific aquarium systems, including optimized fluorescence—which is the emission of light resulting from the absorption of excitation light.

For example, PCT Application Serial No. PCT/SG99/0079, International Publication No. WO 00/49150, by Gong et al., discloses many different types of transgenic fluorescent fish and various methods of producing such fish. Unlike embodiments of the present disclosure, however, the fish disclosed in Gong et al. are genetically modified to provide fluorescence. For instance, Gong et al. discloses zebra fish transfected with green fluorescent protein (GFP) genes isolated from a jelly fish (*Aqueoria Victoria*). In addition, numerous modified mutants of GFP are disclosed, for example, various colors and mammalian optimized mutants are described.

For example, GFP has a maximum excitation at a wavelength of 395 nm and emits green fluorescence at a wavelength (maximum) of 508 nm. The transgenic ornamental fish described in PCT/SG99/0079 are genetically engineered by introducing genes into the fish which express fluorescent proteins.

All patents and patent applications referenced in this application are hereby incorporated by reference herein in their entirety.

SUMMARY OF THE INVENTION

Exemplary embodiments of the present disclosure comprise mollusks with a coating applied to an external shell, where the coating is configured to fluoresce when subjected to a light having a wavelength in a specific range. While coatings have previously been applied to mollusks, such coatings have not been configured to fluoresce at specific ranges for light wavelengths to provide optimal relative brightness of the coating.

Certain embodiments of the present disclosure include a mollusk comprising: a body; an external shell; and a fluorescent coating applied to the external shell. In particular embodiments, the coating can be configured to produce an emitted light when subjected to an excitation light. In specific embodiments, the relative brightness of the coating can be determined by the difference in the intensity of the emitted light from the coating and the intensity of the excitation light, and in some embodiments, the coating can be configured to produce at least 25 percent of the maximum relative brightness of the coating when subjected to a light having a wavelength in a specific range. In particular embodiments, the coating can be configured to produce at least 30 percent, 35 percent, 40 percent, 45 percent, 50 percent, 55 percent, 60 percent, 65 percent, 70 percent or 75 percent of the maximum the relative brightness of the coating when subjected to a light having a wavelength in a specific range.

In specific embodiments, the specific range can include 380 nm to 450 nm, 450 nm to 495 nm, 495 nm to 570 nm, 570 nm to 590 nm, 590 nm to 620 nm, or 620 nm to 750 nm. In some embodiments, the midpoint of the specific range can be approximately 460 nm.

In certain embodiments, the coating can be a paint, and in specific embodiments, the coating can be applied to the shell by brushing the coating onto the shell. In particular embodiments, the coating can be applied to the shell by spraying the coating onto the shell, or by dipping the shell into the coating.

In specific embodiments, the mollusk can be a gastropod, and in certain embodiments, the gastropod can be a snail. In some embodiments, the gastropod can be a member of the family Ampullariidae. The gastropod can be an apple snail or a nerrite snail in certain embodiments.

In particular embodiments, the mollusk can comprise an additional container of the fluorescent coating. In certain embodiments, the fluorescent coating can be non-toxic and not water soluble. In specific embodiments, the fluorescent coating can be applied in a two-stage painting process involving the initial application of non-toxic pigments, followed by a clear top-coat. In certain embodiments, the coating can include a top-coat configured to seal the external shell and attenuate the desiccation of the mollusk. In particular embodiments, the coating can comprise a plurality of layers encompassing an outer lip of the shell, allowing for growth of coating along with the shell.

Specific embodiments can include an aquarium kit suitable for fluorescent ornamental mollusks comprising. In particular embodiments, the aquarium kit can include a tank; a mollusk comprising a coating on an external shell; and an excitation light source. In some embodiments, the excitation light source can be mountable on the tank and the excitation light source can be configured to produce excitation light at a first wavelength that causes the coating to produce an emitted light upon exposure to said excitation light source. In certain embodiments, the relative brightness of the coating can be determined by the difference in the intensity of the emitted light from the coating and the intensity of the excitation light, and the coating and the excitation light source can be configured to produce at least 75 percent of the maximum relative brightness of the coating. In particular embodiments, the coating and the excitation light source are configured to produce at least 25 percent, 30, percent, 35 percent, 40 percent, 45 percent, 50 percent, 55 percent, 60 percent, 65 percent, or 70 percent of the maximum relative brightness of the coating.

In specific embodiments, the light source can be a blue light, a fluorescent light or an ultraviolet light. In particular embodiments, the light source can be configured to emit light with a wavelength in the range of 380 nm to 450 nm, 450 nm to 495 nm, 495 nm to 570 nm, 570 nm to 590 nm, 590 nm to 620 nm, or 620 nm to 750 nm.

In certain embodiments, the aquarium kit can include a second excitation light source which emits light of different wavelength than the first excitation light source.

Particular embodiments can include a method of providing mollusks to the ornamental fish market, where the method comprises: (a) obtaining mollusks comprising a coating configured to produce an emitted light when subjected to an excitation light; and (b) distributing said mollusks to the ornamental fish market. In certain embodiments, the method can also include displaying the mollusks under a blue or ultraviolet light.

In specific embodiments, the method can also include displaying the mollusks under a light having a wavelength of 380 nm to 450 nm, o450 nm to 495 nm, 495 nm to 570 nm, 570 nm to 590 nm, 590 nm to 620 nm or 620 nm to 750 nm.

As used in this specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Any embodiment of any of the present methods, kits, and compositions may consist of or consist essentially of— rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF EXEMPLARY EMBODIMENTS

Figure 1:
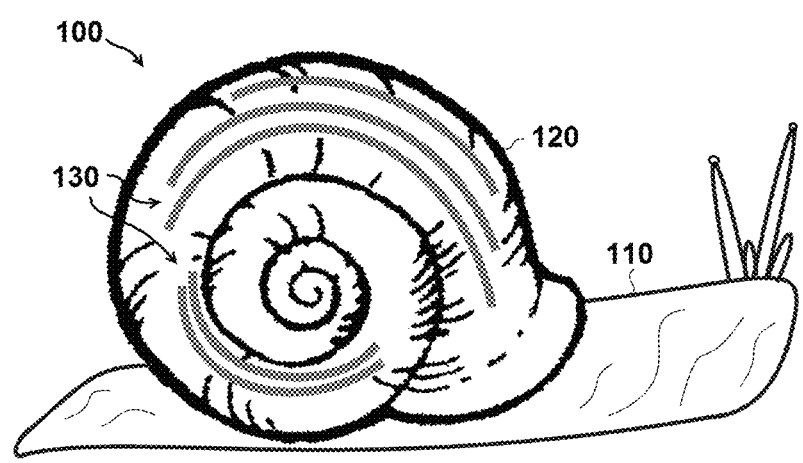
FIG. 1 is a perspective view of a mollusk according to an exemplary embodiment of the present disclosure.

Referring now to FIG. 1, a mollusk 100 comprises a body 110, a shell 120 and a coating 130 applied to shell 120. In exemplary embodiments, coating 130 is configured to fluoresce when subjected to a light having a wavelength in a specific range. In particular embodiments, the coating is a painting that can be applied by brushing the coating onto the shell. In other embodiments, the coating can be sprayed onto the shell, and in still other embodiments, the shell may be dipped into the coating. In exemplary embodiments, coating 130 is non-toxic, not water soluble and is durable long term in an aquarium or other aquatic environment. In specific embodiments, an additional quantity of coating 130 can be provided (e.g. in a "touch-up" bottle) with mollusk 100 to allow coating 130 to be reapplied at a later date should coating 130 be damaged or otherwise affected.

In particular embodiments, coating 130 can be a paint which is selected to adhere well to calcium carbonate or conchiolin, or have particular attributes of cohesion to penetrate and bond well to porous substrates. In certain embodiments, coating 130 can be applied in a two-stage painting process involving the initial application of non-toxic pigments, followed by a clear top-coat for longevity of coating 130, and improved appearance. The application of coating 130 may also comprise an initial non-toxic cleaner or primer to clean and prepare the surface of shell 120, and/or the application of a base coat to provide an even-colored background on which to apply the pigments. In particular embodiments, coating 130 may comprise a top-coat which possesses certain attributes related to reflection, shine, or variegated iridescence. In specific embodiments, coating 130 may include a top-coat which, by action of sealing porous aspects of the shell, attenuates the desiccation of mollusk 100.

As described in more detail below, coating 130 can be configured to produce an emitted light when subjected to an excitation light, where the relative brightness of coating 130 is determined by the difference in the intensity of the emitted light from coating 130 and the intensity of the excitation light. In particular embodiments, the coating can be configured to produce at least 75 percent of the maximum relative brightness of the coating when subjected to a light having a wavelength in a specific range. In other exemplary embodiments, the coating can be configured to produce at least 50, 40 or 25 percent of the maximum relative brightness of the coating when subjected to a light having a wavelength in a specific range In certain embodiments, coating 130 can be a fluorescent red, orange, yellow, green, indigo, violet, blue, purple, pink, or cyan color (or a mixture of one or more of these colors or patterns produced using one or more of these colors). In particular embodiments, coating 130 may be configured to match a fluorescent color of a genetically modified fish, including those disclosed in U.S. Pat. Nos. 7,700,825; 8,232,450; and 8,232,451 and International Publication No. WO 00/49150.

While a discoidal shell is illustrated in the embodiment shown in FIG. 1, it is understood that other embodiments may comprise shells with different configurations, including for example, a cup-shaped shell, a drop-shaped shell, a globose shell and a conical shell. The specific striped configuration of the coating illustrated in FIG. 1 is merely exemplary, and other embodiments may comprise a coating that includes different patterns, e.g. circles, squares, or a coating that covers substantially all of shell 120.

In particular embodiments, coating 130 may comprise designs and patterns that accentuate the natural whorls of the shell, regardless of chirality, including shading, or accent lines. Specific embodiments may incorporate designs for coating 130 intended to provide aesthetic benefit regardless of viewpoint (e.g., apertual, abapertual, umbilical/basal or dorsal). Certain embodiments may include designs of coating 130 which compensate for the continued growth of shell 120 after the initial application of coating 130.

Exemplary embodiments can include, coating (and skipping) whorls in an identifiable pattern of segments (such as alternating) such that the portion of the body whorl closest to the outer lip (near the aperture) would be coated, allowing continued growth of the whorl for some time until it was visually apparent that noticeable growth of shell 120 had occurred.

Additional embodiments may comprise the use of a painting process such as a synthetic rubber paint (including, for example, those sold under the trade name Plasti Dip®) which allows for greater than 400% linear expansion, effectively allowing the paint pattern of coating 120 to grow with shell 130. Exemplary embodiments may also comprise color selections to accent or compliment the color of body 110 and/or shell 120.

Exemplary embodiments can also comprise the application of paints and dyes to shell 120 in such a manner as to protect the dorsal respiratory pore, and other sensitive organs (eye, genital pore, tentacles, foot, etc.) of body 110, with or without the aid of a protective guide.

In particular exemplary embodiments, coating 130 may be applied by electrostatic coating. Certain embodiments may also comprise the application of coating 130 as a synthetic rubber coating, including application of several layers encompassing the outer lip of shell 120, allowing the growth of coating 130 along with shell 120 post-sale to a consumer (e.g. over an extended period of time after coating 130 had initially been applied). Additional embodiments include the application of coating 130 in solid colors and patterns as a vinyl wrapper, allowing the rapid application of complex patterns in a non-toxic coating, and facilitating growth of shell 120 and longevity post-sale.

In exemplary embodiments, mollusk 100 may be a species commonly referred to as a "snail", including more specifically "golden mystery snail" or "apple snail", "nerrite snail", or other species belonging to one of the following families: Ampullariidae, Lymnaeidae, Physidae, Planorbidae, Thiaridae, Viviparidae, and Neritidae.

Exemplary embodiments also comprise an aquarium kit configured for optimizing the appearance of the mollusks with coatings, including those illustrated in FIG. 1 and described above.

Figure 2:
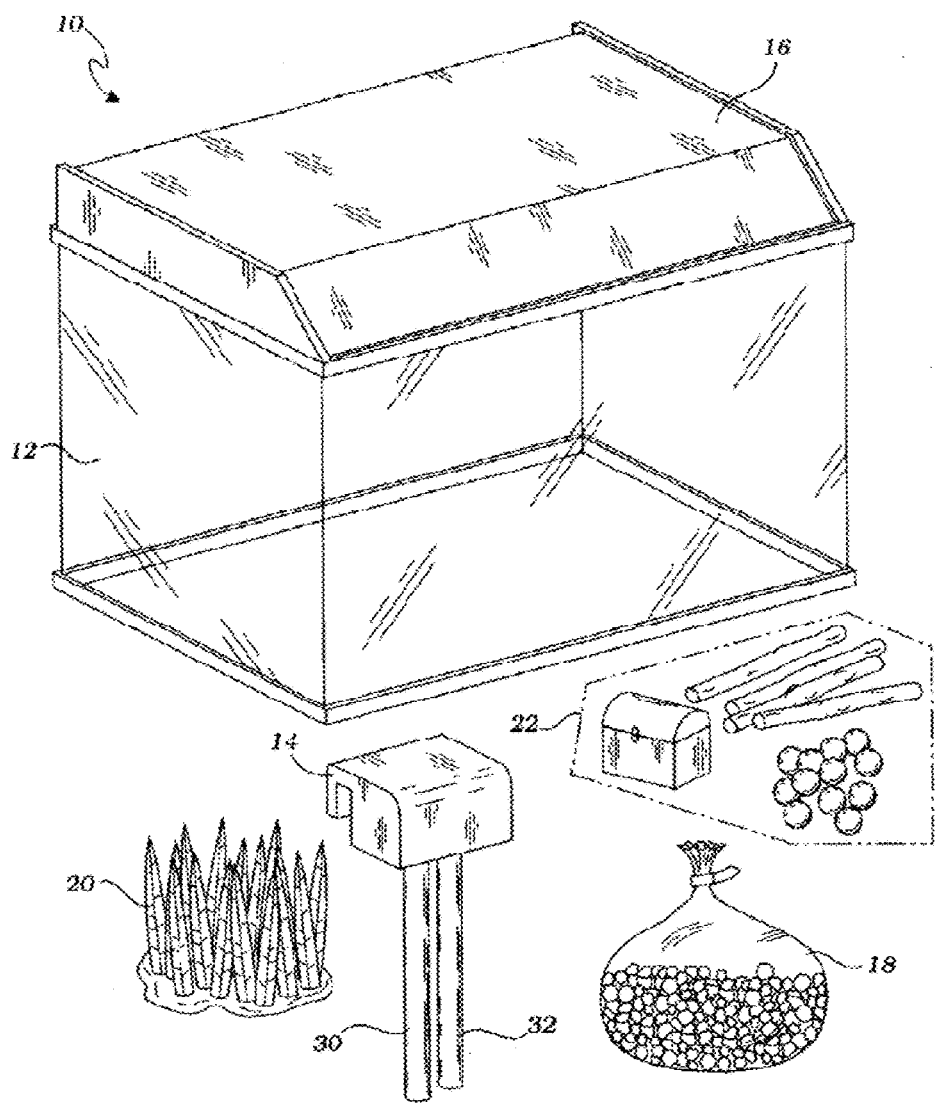
FIG. 2 is a perspective view of a kit configured for use with the embodiment of FIG. 1.

Referring now to FIG. 2, an aquarium kit 10 comprises a tank 12, a water conditioning system 14, and a lighting module 16. Aquarium kit 10 may also comprise various ornamental features such as gravel 18, plants 20 and curios 22. The water condition system 14 may comprise a filter element 30 a heating element 32 and an aeration pump (not shown). The light may be a fluorescent light, a blue light, an ultraviolet light (black light), a xenon lamp, light emitting diode (LED) or other suitable excitation light source.

Figure 3:
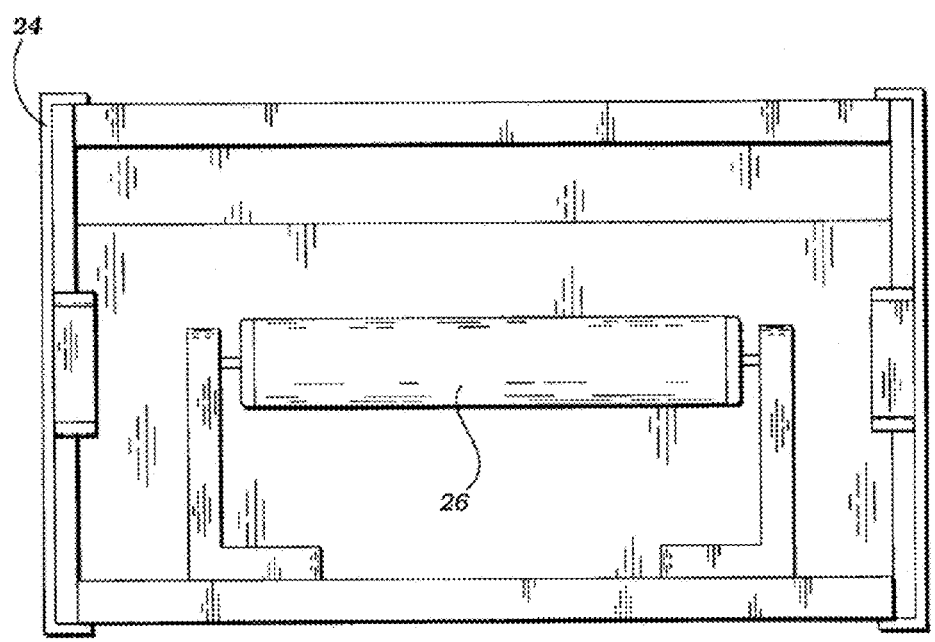
FIG. 3 is a top view of a light module of the kit of FIG. 2.

Turning to FIG. 3, the lighting module 16 comprises a housing 24 and an excitation light source 26. The housing 24 can be configured to rest on the edge of the top of the tank 12. The housing 24 may be designed to cover all or just a portion of the open top of the tank 12. The excitation light source 26 can be mounted to the housing 24. Alternatively, the excitation light source 26 may attach to any part of the tank 12, including the walls of the tank 12 or the top edge of the tank. The excitation light source 26 can be specifically configured to have an emission spectra such that it will be optimal for causing a mollusk with a coating to fluoresce at a level sufficient to be visible to the naked eye upon exposure to the excitation light source.

Fluorescent materials fluoresce upon exposure to excitation light over a range (spectrum) of excitation wavelengths and similarly emit light over a spectrum of wavelengths. In certain embodiments, coating 130 shown in FIG. 1 comprises particular components to provide optimal fluorescence when exposed to excitation light at a specific wavelength or range of wavelengths. For example, coating 130 can be configured to provide the maximum brightness of the emitted fluorescent light relative to the excitation light at a certain wavelength or range of wavelengths.

While a fluorescent material may have a maximum fluorescence at a specific excitation wavelength, such material may not produce the maximum relative brightness of the fluorescence (relative to the excitation light) at that specific wavelength. For example, if the maximum fluorescence occurs at an excitation wavelength that is in the visible range, the visible light can reduce the relative brightness of the emitted fluorescent light. A chart of visible light is shown in Table 1 below:

TABLE 1

| Chart of Colors of Visible Light | |
|---|---|
| Colors of Visible Light | |
| WAVELENGTH (nm) | PERCEIVED COLOR |
| ~390 | Violet |
| ~440 | Blue |
| ~500 | Green |
| ~580 | Yellow |
| ~650 | Red |

Accordingly, the excitation light wavelength that produces the maximum relative brightness for a specific fluorescent compound is the frequency that produces the greatest difference in intensity between the emitted fluorescence and the visible excitation light.

For example, in certain embodiments a black light (emitting ultraviolet light at a wavelength below the visible spectrum) may cause coating 130 to fluoresce, but not at maximum fluorescence. However, for viewing coating 130, the black light may be better than the maximum fluorescence excitation wavelength because the emitted fluorescent light in the visible spectrum will not be outshined by the excitation light. In other exemplary embodiments, coating 130 may be optimized for viewing under a blue light emitting light at a wavelength of approximately 460 nm. It is understood that the embodiments described above are merely exemplary and other embodiments may comprise a coating optimized for viewing under a light emitting different wavelengths, including for example light emitting wavelengths in the range of 380 nm to 450 nm; 450 nm to 495 nm; 495 nm to 570 nm; 570 nm to 590 nm; 590 nm to 620 nm; or 620 nm to 750 nm.

In order to select an excitation light source which is optimal for viewing coating 130 on mollusk 100, the light source should emit light at a wavelength and intensity such that it causes coating 130 to fluoresce, but the source light should also minimize the light produced in the visible spectrum in order to reduce background light.

The relationship between the emitted fluorescent light from coating 130 and the excitation tight can also be defined by a viewing ratio. As used herein, the term "viewing ratio" is defined as the ratio of the intensity of the visible fluorescent light emitted by an object (e.g., coating 130) to the intensity of the visible ambient light within an aquarium tank. In one exemplary embodiment, excitation light source 26 is configured to emit light at a first wavelength spectrum selected to obtain a viewing ratio under a dark external lighting condition of at least 75% of the highest possible viewing ratio for any achievable wavelength spectrum (also defined herein as the "percentage of the maximum viewing ratio") for coating 130. As used herein, the term "dark external lighting condition" is defined herein to mean less than 50 lux.

For example, a laser light source emitting at the maximum excitation wavelength of a fluorescent object and which emits substantially no visible light, would provide for the highest possible viewing ratio. Similarly, a second light source may be configured to emit light at a second wavelength spectrum selected to obtain a viewing ratio of at least 75% of the maximum viewing ratio under a bright external lighting condition. Alternatively, the first and second light sources may provide for a viewing ratio of at least 50%, or at least 40%, or at least 25%, of the maximum viewing ratio for the respective external lighting condition. As used herein, the term "bright external lighting condition" is defined herein to mean greater than 200 lux.

The proper source light may be chosen by knowing the excitation and emission spectrum of the particular fluorescent coating 130 on mollusk 100 and reference to the visible light spectrum. The light source 26 may be activated in any number of ways, including a manual light switch, a push-button toggle, an infra-red remote, a radio frequency remote, an internal or external motion sensor, or a chemical or thermal activator. The light source 26 may also operate in a variety of modes such as fading and transition modes, timer modes or light sensing modes.

In order to enhance the appearance of coating 130 on mollusk 100, aquarium kit 10 may further comprise light filters in or on the tank to block light outside the wavelength of the emission spectra of the particular fluorescent components of coating 130. The appearance of mollusk 100 could also be enhanced using mirrors, one-way films, wavelength-specific or polarizing films, specially angled walls of the tank or the use of special materials within the tank such as reflective mica rocks or such.

In addition, aquarium kit 10 may further comprise multiple excitation light sources 26 wherein the lights may emit different wavelengths, different intensities or different types of light. The tank 12 may have physical separators to maintain certain mollusks in different areas of the tank 12 that are lit by the different light sources 26.

Figure 4:
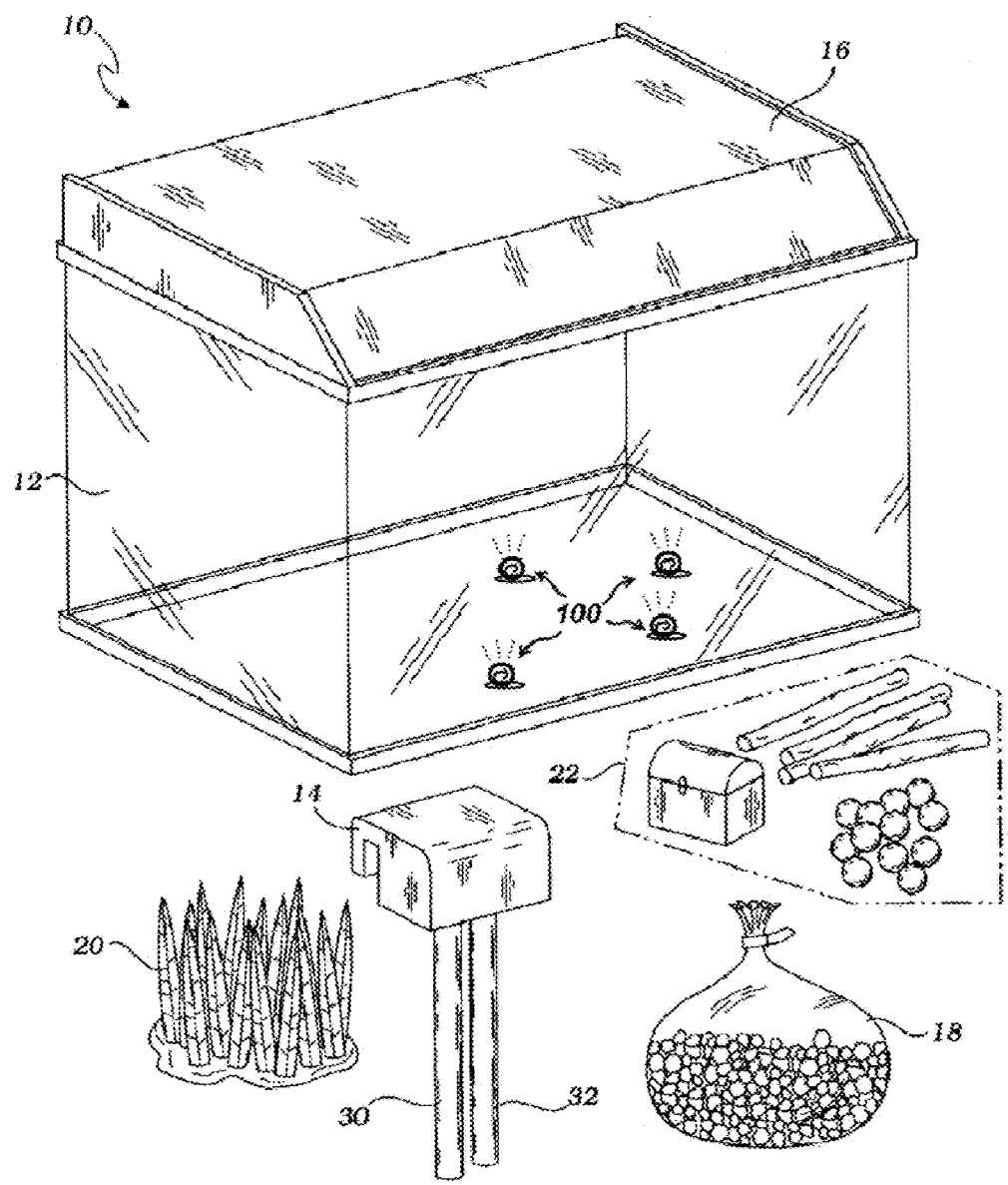
FIG. 4 is a perspective view of the embodiment of FIGS. 1 and 2.

The gravel 18, plants 20 and curios 22 may also be fluorescent to augment the appearance of the aquarium kit 10. For example, the plants 20 may be transgenic or other specialty plants which are fluorescent. The curios 22 can be small items such as a miniature treasure chest, marbles, artificial or actual marine objects like coral, rocks or sticks. As shown in FIG. 4, the aquarium kit 10 may also include a plurality of mollusk 100.

Specific embodiments of the present disclosure further comprise a method of providing mollusks to the ornamental fish market. In specific embodiments, the method comprises: (a) obtaining mollusks comprising a coating configured to produce an emitted light when subjected to an excitation light; and (b) distributing the mollusks to the ornamental fish market. Particular embodiments can further comprise displaying the mollusks under a blue or ultraviolet light. In particular embodiments, the method can further comprise displaying the mollusks under a light having a wavelength of 380 nm to 450 nm, 450 nm to 495 nm, 495 nm to 570 nm, 570 nm to 590 nm, 590 nm to 620 nm, and/or 620 nm to 750 nm.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. No. 7,135,613
U.S. Pat. No. 7,700,825
U.S. Pat. No. 7,834,239
U.S. Patent Publication 2005/0034677
U.S. Patent Publication 2008/0316732
U.S. Patent Publication 2009/0006219
Brem et al. *Aquaculture*, 68:209-219, 1988.
Chourrout et al., *Aquaculture*, 51:143-150, 1986.
Delvin et al., *Nature*, 371:209-210, 1994.
Draper and Moens, In: *The Zebrafish Book*, 5th Ed.; Eugene, University of Oregon Press, 2007.
Du et al., *Bio/Technology*, 10:176-181, 1992.
Innes, W. T., *Exotic Aquarium Fishes*: A work of general reference, Innes Publishing Company, Philadelphia, 1950.
Gross et al., *Aquaculature*, 103:253-273, 1992.
Khoo et al., *Aquaculture*, 107:1-19, 1992.
Lamason et al., *Science*, 310(5755):1782-1786, 2005.
Penman et al., *Aquaculture*, 85:35-50, 1990.
Powers et al., *Mol. Marine Biol. Biotechnol.*, 1:301-308, 1992.
Sin et al., *Aquaculture*, 117:57-69, 1993.
Szelei et al., *Transgenic Res.*, 3:116-119, 1994.
Tsai et al., *Can. J. Fish Aquat. Sci.*, 52:776-787, 1995.
Walker and Streisinger, *Genetics* 103: 125-136, 1983.
Xu et al., *DNA Cell Biol.*, 18, 85-95, 1999.
Zelenin et al., *FEBS Lett.*, 287(1-2):118-120, 1991.
Zhu et al., *Z. Angew. Ichthyol.*, 1:31-34, 1985.

What is claimed is:
1. A mollusk comprising:
a body;
an external shell; and
a fluorescent coating applied to the external shell, wherein:
the coating is configured to fluoresce light when subjected to an excitation light;

the relative brightness of the coating is determined by the difference in the intensity of the fluorescent light from the coating and the intensity of the excitation light; and the coating is configured to produce at least 25 percent of the maximum relative brightness of the coating when subjected to a light having a wavelength in a specific range.

2. The mollusk of claim 1 wherein the coating is configured to produce at least 40 percent of the maximum the relative brightness of the coating when subjected to a light having a wavelength in a specific range.

3. The mollusk of claim 1 wherein the coating is configured to produce at least 50 percent of the maximum the relative brightness of the coating when subjected to a light having a wavelength in a specific range.

4. The mollusk of claim 1 wherein the coating is configured to produce at least 75 percent of the maximum the relative brightness of the coating when subjected to a light having a wavelength in a specific range.

5. The mollusk of claim 1 wherein the specific range includes 380 nm to 450 nm.

6. The mollusk of claim 1 wherein the specific range includes 450 nm to 495 nm.

7. The mollusk of claim 1 wherein the specific range includes 495 nm to 570 nm.

8. The mollusk of claim 1 wherein the specific range includes 570 nm to 590 nm.

9. The mollusk of claim 1 wherein the specific range includes 590 nm to 620 nm.

10. The mollusk of claim 1 wherein the specific range includes 620 nm to 750 nm.

11. The mollusk of claim 1 wherein the midpoint of the specific range is approximately 460 nm.

12. The mollusk of claim 1 wherein the coating is a paint.

13. The mollusk of claim 1 wherein the coating is applied to the shell by brushing the coating onto the shell.

14. The mollusk of claim 1 wherein the coating is applied to the shell by spraying the coating onto the shell.

15. The mollusk of claim 1 wherein the coating is applied to the shell by dipping the shell into the coating.

16. The mollusk of claim 1 wherein the mollusk is a gastropod.

17. The mollusk of claim 13 wherein the gastropod is a snail.

18. An aquarium kit suitable for fluorescent ornamental mollusks comprising:
a tank;
a mollusk comprising a coating configured to fluoresce on an external shell; and
an excitation light source, wherein said excitation light source is mountable on said tank and said excitation light source is configured to produce excitation light at a first wavelength that causes the coating to fluoresce light upon exposure to said excitation light source.

19. The aquarium kit of claim 18 wherein:
the relative brightness of the coating is determined by the difference in the intensity of the fluorescent light from the coating and the intensity of the excitation light;
the coating and the excitation light source are configured to produce at least 75 percent of the maximum relative brightness of the coating.

* * * * *